(12) United States Patent
Friedman

(10) Patent No.: US 6,544,530 B1
(45) Date of Patent: Apr. 8, 2003

(54) STABLE OIL-IN-GLYCERIN EMULSION

(75) Inventor: Doron Friedman, Karme Yosef (IL)

(73) Assignee: J.P.M.E.D. Ltd., Karme Yosef (IL)

( * ) Notice: Subject to any disclaimer, the term of this patent is extended or adjusted under 35 U.S.C. 154(b) by 0 days.

(21) Appl. No.: 09/700,862

(22) PCT Filed: Mar. 9, 2000

(86) PCT No.: PCT/IL00/00142

§ 371 (c)(1),
(2), (4) Date: Jan. 22, 2001

(87) PCT Pub. No.: WO00/56346

PCT Pub. Date: Sep. 28, 2000

(30) Foreign Application Priority Data

Mar. 22, 1999 (IL) .................................................. 129102

(51) Int. Cl.[7] .......................... A61K 9/00; A01N 25/00; A01N 65/00

(52) U.S. Cl. ........................ 424/400; 424/725; 424/405; 424/434; 514/886; 514/937

(58) Field of Search ................................ 424/725, 400, 424/405, 434; 514/886, 937

(56) References Cited

U.S. PATENT DOCUMENTS 5,329,881 A * 7/1994 O'Rourke
5,350,773 A * 9/1994 Schweikert et al.
6,193,987 B1 * 2/2001 Harbeck et al.

* cited by examiner

Primary Examiner—Christopher R. Tate
Assistant Examiner—Randall Winston
(74) Attorney, Agent, or Firm—Townsend & Townsend & Crew LLP

(57) ABSTRACT

The invention provides a composition of matter comprising a stable oil-in-glycerin emulstion containing at least one oil, at least one emulsifier and glycerin.

20 Claims, No Drawings

STABLE OIL-IN-GLYCERIN EMULSION

CROSS REFERENCES TO RELATED APPLICATIONS

This application is a §371 national stage filing of PCT/IL00/00142 filed Mar. 9, 2000, and claims the benefit of priority from Israel patent application IL 129102, filed Mar. 22, 1999, the full disclosures of which are incorporated herein by reference.

TECHNICAL FIELD

The present invention relates to a stable oil-in-glycerin emulsion.

BACKGROUND ART

Oil-in-water emulsions and water-in-oil emulsions are well-known in the art.

Emulsions are thermodynamically non-stable dispersions systems containing two immiscible liquids. A large amount of energy is required to rupture an internal phase of a liquid into small droplets producing very large surface and interfacial free energy. This free energy is the driving force for reuniting the droplets, a phenomenon leading to phase separation and the breakdown of the emulsion. Instability in emulsions is characterized as coalescence, creaming and finally phase separation. Coalescence is the unification of suspended droplets where larger droplets are produced from smaller ones. Creaming is the migration of particles (usually in an upward direction), due to differences of specific weight between internal and external phases. Creaming brings many droplets closer together, thereby increasing coalescence. Coalescence, in turn, increases creaming since larger droplets migrate at a quicker rate. Coalescence is irreversible while creaming may be reversible. Phase separation is the final stage of emulsion break.

Stable emulsions coalescence and cream at a very low rate. The low rate allows for an adequate shelf life of an emulsion. Emulsions are considered stable if no phase separation is detected for a defined period of time and conditions and if creaming occurs, it is practically reversible.

Many emulsion classifications are described in the literature. Basic emulsions are classified by the type of liquid constituting the internal or external phases. The classical types are oil-in-water or water-in-oil emulsions. Cosmetic emulsions, for example, are named according to their use: cold cream, absorbing creams, night creams, vanishing cream, moisturizing creams, lotions, etc.

Known emulsions are routinely used as a delivery vehicle of active substances. However, said vehicle is not optimal for the proper delivery of all types of active substances.

Known emulsions are not optimal, for example, in the delivery of essential oils.

Essential oils are potent bioactive herbal extracts which are regularly utilized in the practice of phytomedicine, aromatherapy and homeopathy. Essential oils are also used as food additives and in spices. Essential oils are hydrophobic and practically insoluble in water or glycerin. Said oils are, however, soluble in alcohols such as ethyl alcohol and isopropanol and in oils such as tryglycerides and organic solvents such as acetone. In light of the above, essential oils are regularly and traditionally dispensed in vegetable tryglyceride oils or alcohol. Dispersion of essential oils in water is possible through the utilization of ample amounts of surfactant solubilizers or emulsifiers, however these solutions tend to be unstable.

The delivery of essential oils within pure oils such as vegetable tryglyceride oils is possible, but is not always optimal. For example, the use of oils within the oral cavity or on the scalp is not pleasant and undesirable due to the oily remnant and the need for removal of said remnant with soap.

A further drawback of known delivery vehicles is the presence of alcohol therein.

Recent scientific data suggests that alcohol may play a role in toxic and genotoxic biological effects. Consumers are therefore refraining from using products containing alcohol, especially for sensitive body organs such as for the oral cavity and babies' skin. Alcohol is an irritant to the skin, scalp, mucous membrane and gastrointestine. In the oral cavity alcohol has a foul taste which is especially unpleasant for young and elderly people. Alcohol burns tissues in a way that delays tissue healing after skin traumas. Alcohol dehydrates the skin, mucous membrane and tissues, which dehydration causes discomfort and pain. Therefore medical research is investing in finding alcohol free medicaments.

DISCLOSURE OF THE INVENTION

In light of the above, the present invention provides a stable oil-in-glycerin emulsion that can perform as an adequate storage and delivery vehicle for bioactive, water insoluble active ingredients, including essential oils.

According to the present invention there is provided a composition of matter comprising a stable oil-in-glycerin emulsion containing at least one oil, at least one emulsifier and glycerin.

In a preferred embodiment there is provided a composition of matter wherein the emulsion further comprises at least one bioactive component, wherein said bioactive component is selected from the group consisting of a plant extract, an essential oil, and an oleoresin.

The present invention also provides a composition of matter wherein said emulsion is substantially alcohol free.

In a preferred embodiment of the present invention said oil is selected from the group consisting of at least one mineral oil, at least one vegetable oil, at least one water insoluble botanical extract and mixtures thereof wherein said vegetable oil is a vegetable tryglyceride, wherein said vegetable tryglyceride is a medium chain tryglyceride, wherein said medium chain tryglyceride is a capric-caprylic tryglyceride and wherein said capric-caprylic tryglyceride is fractionated coconut oil.

In a most preferred embodiment said oil is selected from the group consisting of a plant extract, an essential oil, and an oleoresin and functions also as an active ingredient.

In another preferred embodiment said mineral oil is a paraffin oil.

In preferred embodiments of the present invention the following quantities are preferable:

a) said vegetable tryglyceride is present in an amount ranging from about 1–40 wt/wt %, or from 2–20 wt/wt %;

b) said emulsifier is present in an amount ranging from about 0.1–20 wt/wt %, or from about 0.1–5 wt/wt %; and c) said bioactive component is present in an amount ranging from about 0.1–20 wt/wt %.

In a most preferred embodiment said emulsifier biodegradable (i.e., degradable in the human body and the environment) and/or is substantially free of polyoxyethylene.

In a most preferred embodiment of the present invention said bioactive component is water insoluble.

In an even further preferred embodiment of the present invention said glycerin constitutes a continuous phase of said emulsion and a minor portion of water is included in said glycerin phase.

It is important to note that the botanical extract of the present invention may have has anti-inflammatory, anti-bacterial, anti-parasitic, anti-viral, immunity modulation and/or stress relaxant properties.

It also should be noted that the emulsifier of the present invention may be one of the following:

a) a fatty acid conjugated to a natural hydrophilic molecule;
b) a fatty alcohol conjugated to a natural hydrophilic molecule;
c) an ester of fatty acid/s and carbohydrates or polycarbohydrate saccharides; and
d) an ether of fatty alcohol/s and carbohydrates or polycarbohydrate saccharides.

In a preferred aspect of the invention, the combination of an oil-in-glycerin emulsion and a plant extract enables the dispersion of a water insoluble bioactive component in a biocompatible, safe and convenient dosage form, while avoiding the disadvantages associated with classical vehicles.

The oil-in-glycerin emulsions are pleasant for use on the skin and on mucous membranes such as the oral cavity, ears and scalp. Additionally, the emulsions of the present invention are well accepted organoleptically and physiologically, hence, offering good patient compliance. The oil-in-glycerin emulsions are easy to apply, as well as being easy to remove after the substantial absorption thereof. Stable oil-in-glycerin emulsions containing essential oils are advantageous for obtaining physical and chemical stability of essential oil compositions.

As will be realized, the present invention provides an emulsion which is alcohol free, has a prolonged shelf life and improved heat stability for withstanding elevated temperatures during a long period of time. Furthermore, the oil-in-emulsion resists sub-zerotemperatures, it is stable upon freezing and does not break at minus 20° C. Thaw of oil-in-glycerin emulsions is simple and does not affect original properties.

While many publications exist in which glycerin, oils and emulsifiers are mentioned as possible components, no publication has been found teaching or suggesting a stable oil-in-glycerin emulsion of the type defined and claimed herein.

Thus, e.g., in U.S. Pat. No. 5,980,925 there is described an anchoring agent or dermal anchoring/substantive agent that enhances the activity of active ingredients, such as antimicorbial agents like chlorhexidine gluconate. Glycerin is mentioned in this patent as an example of such an active anchoring agent that has the desired bioactivity.

While said patent teaches gels and creams having a glycerin content, there is no referral in said patent to a stable oil-in-glycerin emulsion and there is no referral to solubilizing a poorly water-soluble or water insoluble compounds or hydrophobic compounds.

Practically, the glycerin may also be incorporated in a cream for the purpose of enhancing the activity of antimicrobial compounds, however the patent does not teach or suggest a dispersion system of oil droplets dispersed and stabilized in glycerin.

Oil-in-glycerin emulsions are easily prepared. It is possible to produce coarse oil-in-glycerin emulsions of 10 to 50 microns droplet size with simple stirring and without resort to the use of high shear mixers. It is also easy to control droplet size by the utilization of appropriate mixing equipment and energy input. Fine oil-in-glycerin emulsions, having a mean droplet size of five micron, are achieved with a conventional "Silverson" type mixer at moderate speed and a short duration of mixing. High speed "Silverson" type mixing is sufficient to obtain emulsions containing 500 to 3000 nanometers (0.5 to 3 microns) droplets. Further reduction of droplet size is possible by applying appropriate equipment of high pressure and high shear output.

The present invention relates to oil-in-glycerin emulsions in which the oil is the internal phase and the glycerin is the external, continuous phase. The phase inversion ratio varies markedly according to the following variables: emulsifier type, oil nature, temperature and the various additives and said variables are chosen to support condition for an oil-in-glycerin emulsion. Thus, the amount of emulsifier or emulsifiers should be adjusted to the internal oil volume ratio and more emulsifier is needed when a larger ratio of oily phase is present. Properly formulated oil-in-glycerin emulsions may contain up to equal parts of oil and glycerin phases.

The oil-in-glycerin emulsions of the present invention are well suited for pharmaceutical, complementary medicine, cosmetic, nutraceutical and veterinary use, as well as for topical external use on skin or mucous membrane and internal oral consumption.

A botanical essential oil is a volatile mixture of esters, aldehydes, alcohols, ketones and terpenes, which is prepared from botanical materials or plant cell bio-mass from cell culture. Examples of essential oils include, but are not limited to, oil of cinnamon, prepared from the dried bark of the roots of *Cinnamomum zeyloriaceae*; cajeput oil, eucalyptus oil, prepared from the fresh leaves and branches of various species of Eucalyptus, such as *E. globulus*; fennel oil, prepared from dried ripe fruit of *Foeniculum vulgare*; geranium oil, prepared from the aerial parts of Pelargonium species; girofle oil, lavander oil, prepared from fresh flowering tops of Lavandula species such as *Lavandula officinalis*; lemon oil, obtained from the fresh peel of *Citrus lemon*; spearmint oil, prepared from the aboveground parts of fresh flowering Mentha species, such as *M. spicata*; myrte oil, origano oil, pine oil, rosemary oil, prepared from tops or leafy twigs of *Rosmarinus officinalis*; sarriette oil, thyme oil, prepared from the leaves and flowering tops of *Thymus vulgaris*; and tea-tree oil, obtained from the leaves of *Melaleuca olternifolia*. Hypericum oil, Pinus, Star anise seeds oil and Garlic oil (*Allium sativum oil*).

Alcohol free herbal extracts are extracts of plant materials, such as a tincture of botanical materials, which are prepared by contacting botanical material with a solvent [*British Herbal Pharmacopeia*, Peter R. Bradley, ed., British Herbal Medicine Association, 1983; and *British Herbal Compendium*, Peter R. Bradley, ed., British Herbal Medicine Association, 1992]. The solvent can be aqueous or organic, or a combination thereof. The most preferred solvents are hydroalcoholic solvents as defined in *British Herbal Pharmacopoeia and Compendium*. The extracts containing alcohol are further processed and alcohol is evaporated and removed by lyophilization, spray drying, simple evaporation by heat or under vacuum. The dry product mass is further solubilized and dissolved in an appropriate, glycerin water mixture. The botanical material can include, but is not limited to, one or more of the following species: Plantago (*Plantago major*), Hypericum (*Hypericaceae perforatus*), Echinacea (also known as Coneflower) (Echinaceae species such as *Echinaceae angustifoliae radix* and *Echinaceae*

*purpurea*), Baptisia, Calendula, Myrrh, Phytolaca, Salvia, Catechu black, Krameria, Tsuga, Rosmarinus, Styrax, Crataegus, Glycerrhiza (*Glycerrhiza glabra*), Angelica, Krameria, Matricaria, Mallow and Sage. Chamomile, Hammamelis, Aloe vera, Nettle (Urtica). Kava Kava, Noni fruit (*Morinda citrifolia*), Feverfew (*Tanacetum parthenolide*), Astragulus.

An emulsifier is a surface active agent or protective colloid that is capable of suspending the oily phase and stabilizing the emulsion by coating the oil droplets and avoiding the separation of the internal oily phase. The film coat produced by the emulsifier is a barrier between the immiscible phase and also prevents droplets association, coagulation and coalescence. Examples of emulsifier include, but are not limited to, non-ionic surface active agents of polyethyleneglycol derivatives conjugated via ether or ester bond to one or more free fatty acids or sorbitans or fatty acids sorbitan conjugares or carbohydrates or mono or di glycerides or block copolymers with polyoxypropylene, such as, Tween 80 (polyoxyethylebe sorbitan monooleate) and Tween 20 (polyoxyethylene sorbitan monolaurate). Fatty acids conjugated to carbohydrates or sugars or polysugars, such as cetearyl glucoside or polyglucosides or sorbitan monooleate (Span 80) or sorbitan monolaurate (Span 20) or polyoxyethylene monostearate (Myrj 45) or polyoxyethylene vegetable oil (Emulphor). Cationic or anionic surfactants, such as sodium sulfated alkyls, (sodium lauryl sulfate), triethanol-amine oleate, cetyl piridinium chloride. Amphotheric surfactants, such as proteineted fatty acids, amido-betaine and fatty acids conjugates. Protective colloids such as polysaccharides gums, Xanthan gums, Tragacanth, Gum arabica, Acacia, or proteins or conjugated proteins capable of forming and protecting stable oil in glycerin emulsion.

Typical oil-in-glycerin emulsions are characterized by having viscosity of 15,000 to 25,000 centipoise and neutonian flow. Viscosity may be reduced by the addition of water. The oil-in-glycerin emulsion viscosity may be controlled by addition of viscosity forming agents, such as, carbomers, carbopol, cellulose derivatives or natural gums, such as Xanthan gum or colloidal fumed silica. Semi-solid oil-in-glycerin emulsions are suitable for topical and mucosal application, for effective local delivery of water insoluble bioactives. Oil-in-glycerin emulsions are advantageous for oral administration to achieve enhanced oral bioavailability for hydrophobic bioactives. Oil-in-glycerin emulsions may be used orally in a viscous fluid state, syrup like form, or within soft gelatin capsules.

An oil-in-glycerin emulsion having a low oil to glycerin ratio (R<10) tends to cream. When creaming takes place at 15° C. It may occur during a period ranging from days to weeks. At 35° C. the period is shorter, ranging between hours and days. It should be noted that creaming ia reversible process. In cases where creaming or reversible separation has occurred, re-dispersion is achieved by light shaking. An oil-in-glycerin emulsion having a high ratio (R>10), may not cream even after several weeks at a temperature of 35 C. The creaming mentioned above is also influenced by the amount and type of bioactives. For example, hammamelis fluid extract glycerin effects faster creaming in comparison to aloe vera or echinacea fluid extract glycerin. Some essential oils influence the stability of an emulsion, while others do not.

Oil-in-glycerin emulsions are easily and readily diluted with water. The glycerin is dissolved in the water and the oily phase stays emulsified for as long as twenty four hours, resulting in stable oil-in-water/glycerin emulsion which is ready to use.

Oil-in-glycerin emulsions are suitable for use in humans and animals, on skin, scalp, mucous membrane, ear instillation, oral rinse, and for oral consumption. The emulsions the present invention are applicable to the nose and eyes only after dilution with water, since glycerin is not physiologically acceptable at high concentrations.

The oil-in-glycerin emulsions are basically neutonian and flow easily out of any commercial consumer product orifice opening or dropper. Oil-in-glycerin emulsions may be packaged in glass, aluminum or plastic containers.

Viscosity is easily controlled by the addition of viscosity agents to produce gels for use as rectal or vaginal inserts. Oil-in-glycerin emulsion are readily incorporated into semi-solid creams. Oil-in-glycerin emulsions may be encapsulated in soft gelatin capsules. Oil-in-glycerin emulsions may be used as syrups for oral consumption.

Oil-in-glycerin emulsions may contain high surfactant levels to promote foam and cleaning effects in shampoos and mouthwashes.

The oily phase is preferably liquid lipids but may also contain solid lipids alone or in combination with liquid lipids. The amount of required emulsifier to stabilize the emulsion depends on the amount and type of oily phase and emulsifier. Generally, 0.5% to 2% are adequate to stabilize oil-in-glycerin emulsions. The more suitable surfactants for oil-in-glycerin emulsions have a hydrophilic moiety of carbohydrate or polyethylene type, such as sugar, polysugar, polyethyleneoxide or polyglycerols and derivatives or combinations thereof such as sorbitan polyethylene oxides. The hydrophobic moiety of the surfactants mentioned above is preferably a fatty acid or alcohol having a 10–18 carbon chain.

Phospholipids may be added to oil-in-glycerin emulsions, however, phospholipids alone are not sufficient emulsifiers to stabilize many oil-in-glycerin emulsions.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

The oily and glycerin phases are heated separately to 70° C. until all ingredients melt and are well dissolved. The phases are combined while mixing. Mixing may be performed with any mixer, blender, homogenizer, etc. which is used for producing emulsions. Oil-in-glycerin emulsions may also be prepared by heating all the ingredients, including oil, glycerin and emulsifiers, except for heat sensitive bioactives, in a single batch, mixing to achieve melting of solids and with continued mixing until cooled to room temperature, with the addition of any heat sensitive bioactives to the cooling mixture.

The oil-in-glycerin emulsions presented herein in the following examples are stable for an adequate period of time. The following examples are to demonstrate various compositions that do not undergo phase separation or breakdown for at least one year at room temperature and for many days or weeks at 35° C. Oil-in-glycerin emulsions that cream within this time are easily redispersed while maintaining original properties. Redispersion of the present oil-inglycerin emulsions is easily performed by gentle shaking of the sample for a short period of time.

DESCRIPTION OF PREFERRED EMBODIMENTS

Example 1

Oil-in-glycerin Liquid Emulsion; Plain Base

| Ingredient | % W/W |
|---|---|
| Glycerin | 84.0 |
| Medium chain trygliceride (MCT) oil | 15.0 |
| Cetearyl-glucoside | 1.0 |

Example 2

Oil-in-glycerin Emulsion; Plain Natural Base

| Ingredient | % W/W |
|---|---|
| Glycerin | 81.6 |
| Medium chain trygliceride (MCT) oil | 15.0 |
| Cetearyl-oil | 1.0 |
| Mono-di-glycerides | 1.0 |
| Oleic acid | 0.2 |
| Beeswax | 1.0 |
| Xanthan gum | 0.2 |

Example 3

Oil-in-glycerin Emulsion; Cleansing and Foaming Base

| Ingredient | % W/W |
|---|---|
| Glycerin | 80.5 |
| MCT oil | 11.0 |
| Jojoba oil | 4.0 |
| Decyl-glucoside | 2.0 |
| Cocamidopropylbetaine | 2.0 |
| Vitamin E acetate | 0.5 |

Example 4

Oil-in-glycerin Emulsion Liquid Base with Preservatives

| Ingredient | % W/W |
|---|---|
| Glycerin | 83.3 |
| MCT oil | 15.0 |
| Cetearyl-glucoside | 1.0 |
| Vitamin E acetate | 0.5 |
| Propyl paraben | 0.1 |
| Methyl paraben | 0.1 |

Example 5

Ear Drops

| Ingredient | % W/W |
|---|---|
| Glycerin | 84.3 |
| MCT oil | 12.0 |
| Cetearyl-glucoside | 1.0 |
| Vitamin E acetate | 0.5 |
| Eucalyptus oil | 1.0 |
| Thyme oil | 0.5 |
| Hpericum oil | 0.5 |
| Chamomile dry extract | 0.2 |

Example 6

Ear Drops

| Ingredient | % W/W |
|---|---|
| Glycerin | 83.3 |
| MCT oil | 12.0 |
| Tween 80 | 2.0 |
| Vitamin E acetate | 0.5 |
| Eucalyptus oil | 1.0 |
| Thyme oil | 0.5 |
| Hpericum oil | 0.5 |
| Chamomile dry extract | 0.2 |

Example 7

Ear Drops

| Ingredient | % W/W |
|---|---|
| Glycerin | 80.3 |
| MCT oil | 12.0 |
| Echinacea fluid extract glycerin | 2.0 |
| Aloe vera fluid extract glycerin | 2.0 |
| Cetearyl-glucoside | 1.0 |
| Vitamin E acetate | 0.5 |
| Eucalyptus oil | 1.0 |
| Thyme oil | 0.5 |
| Hpericum oil | 0.5 |
| Chamomile dry extract | 0.2 |

Ear drops vehicles should be non-alcoholic and preferably without water since water enhances bacterial proliferation. Too much water in the ears may lead to swimmer's ear syndrome. Examples 5 to 7 are therefore most preferred ear drops vehicles, enabling good delivery of hydrophobic bioactives as well as hydrophilic bioactives to the ear without water or alcohol.

Example 8

Anti-lice: Hair, Scalp and Body Treatment

| Ingredient | % W/W |
| --- | --- |
| Glycerin | 78.5 |
| MCT oil | 10.0 |
| Cetearyl-glucoside | 1.5 |
| Beeswax | 0.5 |
| Vitamin E acetate | 0.5 |
| Star anise oil | 3.0 |
| Eucalyptus oil | 3.0 |
| Rosemarine oil | 3.0 |

Essential oils are used traditionally to expel lice by killing the lice and preventing recurrent contamination. The anti-lice oil-in-glycerin emulsion containing essential oils is non-greasy, easy to clean and alcohol free.

Example 9

Oral Rinse, Anti Plaque Concentrated Wash for Dilution

| Ingredient | % W/W |
| --- | --- |
| Glycerin | 80.3 |
| MCT oil | 12.0 |
| Tween 80 | 2.0 |
| Vitamin E acetate | 0.5 |
| Eucalyptus oil | 3.0 |
| Thyme oil | 1.0 |
| Cinnamon oil | 1.0 |
| Chamomile dry extract | 0.2 |
| Sodium fluoride | 1.5 |
| Chlorohexidine digluconate | 0.05 |

The concentrated viscous liquid according to the present invention as set forth in this example is intended for dilution five to ten times with tap water by the user before use. The dilution and mixing with water is instantaneous requiring only a few seconds of gentle swirling of the glass. The diluted solution is pleasant for a mouthwash or breath refresher and may be formulated with or without fluoride and in various flavors to suit various populations' preferences.

Example 10

Oral Rinse, Anti Fungal & Aphtous, Concentrated Wash for Dilution

| Ingredient | % W/W |
| --- | --- |
| Glycerin | 81.3 |
| MCT oil | 12.0 |
| Cetearyl-glucoside | 1.5 |
| Vitamin E acetate | 0.5 |
| Eucalyptus oil | 0.5 |
| Thyme oil | 0.5 |
| Cinnamon oil | 0.5 |
| Tea-tree oil | 0.5 |
| Hypericum oil | 0.5 |
| Chamomile dry extract | 0.2 |
| Echinacea fluid extract glycerin | 2.0 |

Essential oils are potent anti-bacterials used traditionally for oral hygiene and treating gums diseases. The oil-in-glycerin emulsion mouthwashes of examples 9 and 10 are typical examples for oil-in-glycerin emulsions which must be diluted prior to use.

Example 11

Oral Toothpaste

| Ingredient | % W/W |
| --- | --- |
| Glycerin | 61.8 |
| Fumed silica | 20.0 |
| MCT Oil | 12.0 |
| Tween 80 | 2.0 |
| Sodium lauryl sulphate | 1.0 |
| Vitamin E acetate | 0.5 |
| Eucalyptus oil | 1.0 |
| Thyme oil | 1.0 |
| Cinnamon oil | 0.5 |
| Chamomile dry extract | 0.2 |
| Sodium fluoride | 0.15 |

Addition of solid powder may convert viscous liquid oil-in-glycerin emulsions into semi-solid paste such as toothpaste. It is possible to obtain regular as well as transparent or gel toothpaste.

Example 12

Topical Skin Application, Mosquitoes Repellent

| Ingredient | % W/W |
| --- | --- |
| Glycerin | 76.8 |
| MCT oil | 12.0 |
| Cetearyl-glucoside | 4.0 |
| Cetearyl octanoate | 4.0 |
| Xanthan gum | 1.5 |
| Vitamin E acetate | 0.5 |
| Eucalyptus oil | 0.5 |
| Thyme oil | 0.5 |
| Geranium oil | 0.5 |
| Hpericum oil | 0.5 |
| Rosmarinus oil | 0.5 |
| Aloe vera dry extract | 0.2 |

Example 13

Topical Skin Application, Anti-acne

| Ingredient | % W/W |
| --- | --- |
| Glycerin | 76.8 |
| MCT oil | 12.0 |
| Cetearyl-glucoside | 4.0 |

-continued

| Ingredient | % W/W |
|---|---|
| Cetearyl octanoate | 4.0 |
| Xanthan gum | 1.5 |
| Vitamin E acetate | 0.5 |
| Eucalyptus oil | 0.5 |
| Thyme oil | 0.5 |
| Geranium oil | 0.5 |
| Rosmarinus oil | 0.5 |
| Aloe vera dry extract | 0.2 |
| Hypericum dry extract | 0.2 |

Example 14

Topical Skin Application, Anti-wart (Veruca)

| Ingredient | % W/W |
|---|---|
| Glycerin | 74.8 |
| MCT oil | 10.0 |
| Cetearyl-glucoside | 4.0 |
| Cetearyl octanoate | 4.0 |
| Xanthan gum | 1.5 |
| Garlic oil | 1.0 |
| Citronella oil | 1.0 |
| Hpericum oil | 1.0 |
| Vltamin E acetate | 0.5 |
| Sanguinaria dry extract | 0.5 |
| Thuja occidentalis dry extract | 0.5 |
| Aloe vera dry extract | 0.2 |

Example 15

Topical Skin Application, Anti-fungal

| Ingredient | % W/W |
|---|---|
| Glycerin | 71.3 |
| MCT oil | 10.0 |
| Beeswax | 6.0 |
| Cetearyl-glucoside | 5.0 |
| Phytolaca fluid extract glycerin | 2.0 |
| Echinacea fluid extract glycerin | 2.0 |
| Xanthan gum | 1.5 |
| Vitamin E acetate | 0.5 |
| Geranium oil | 0.5 |
| Hpericum oil | 0.5 |
| Tea-tree oil | 0.5 |
| Aloe vera dry extract | 0.2 |

Examples 11 to 15 are presented to demonstrate semi-solid cream type oil-in-glycerin emulsions.

Example 16

Topical Skin Application, Muscles and Joints Pain Relief

| Ingredient | % W/W |
|---|---|
| Glycerin | 71.3 |
| MCT oil | 10.0 |
| Beeswax | 6.0 |
| Cetearyl-glucoside | 5.0 |
| Xanthan gum | 1.5 |
| Vitamin E acetate | 0.5 |
| Rosmarinus oil | 1.0 |
| Lavendula (thyme)oil | 1.0 |
| Harpagophytum dry extract | 1 |
| Hmmamelis dry extract | 1 |
| Arnica dry extract | 1 |

Example 17

Lip Balsam, For Cracked Lips

| Ingredient | % W/W |
|---|---|
| Glycerin | 68.3 |
| MCT Oil | 10.0 |
| Cetearyl alcohol | 6.0 |
| Beeswax | 6.0 |
| Cetearyl-glucoside | 5.0 |
| Xanthan gum | 1.5 |
| Vitamin E acetate | 0.5 |
| Eucalyptus oil | 0.5 |
| Thyme oil | 0.5 |
| Geranium oil | 0.5 |
| Hpericum oil | 0.5 |
| Rosmarinus oil | 0.5 |
| Aloe vera dry extract | 0.2 |

Example 18

Mucosal Application, Concentrated Vaginal Hygiene

| Ingredient | % W/W |
|---|---|
| Glycerin | 81.0 |
| MCT oil | 12.0 |
| Cetearyl-glucoside | 1.0 |
| Tween 80 | 2.0 |
| Vitamin E acetate | 0.5 |
| Eucalyptus oil | 1.0 |
| Thyme oil | 0.5 |
| Hpericum oil | 0.5 |
| Geranium oil | 0.5 |
| Chamomile dry extract | 0.5 |
| Aloe vera dry extract | 0.5 |

This is a concentrated product which may be diluted by the user three to five times with water before use.

Example 19

Mucosal Application, Anti-hemorrhoid

| Ingredient | % W/W |
|---|---|
| Glycerin | 80.0 |
| MCT oil | 7.0 |
| Cetearyl-glucoside | 4.0 |
| Cetearyl-octanoate | 4.0 |
| Vitamin E acetate | 0.5 |
| Thyme oil | 0.5 |
| Hpericum oil | 0.5 |
| Geranium oil | 0.5 |
| Tea-tree oil | 0.5 |
| Propolis | 0.5 |
| Hammamelis dry extract | 0.5 |
| Echinacea dry extract | 0.5 |
| Calendula dry extract | 0.5 |
| Comfrey dry extract | 0.5 |

Example 20

Alcohol Free Vehicle for Oral Use of Poor Water Soluble Bioactives

| Ingredient | % W/W |
|---|---|
| Glycerin | 80.5 |
| MCT oil | 15.0 |
| Cetearyl-glucoside | 1.0 |
| Lecithin | 1.5 |
| Vitamin E acetate | 0.5 |
| Dry powder bioactive | 1.0 |

Example 21

Alcohol Free Vehicle for Oral Use of Poor Water Soluble Bioactives

| Ingredient | % W/W |
|---|---|
| Glycerin | 80.5 |
| MCT oil | 12.0 |
| Cetearyl-glucoside | 1.0 |
| Tween 80 | 1.0 |
| Vitamin E acetate | 0.5 |
| Liquid or liquid extract bioactive | 5.0 |

Example 22

Oral Oil-in-glycerin in Soft Gelatin Capsules

| Ingredient | % W/W |
|---|---|
| Glycerin | 64.5 |
| MCT oil | 30.0 |
| Cetearyl-glucoside | 2.0 |
| Mono-di-glycerides | 2.0 |
| Vitamin E acetate | 0.5 |
| Leucopens | 0.5 |
| Carotenoids | 0.5 |

Example 23

Oral Syrup Like, Liquid Oil-in-glycerin emulsion

| Ingredient | % W/W |
|---|---|
| Glycerin | 80.5 |
| MCT oil | 15.0 |
| Sugar esters (E473) | 2.0 |
| Vitamin E acetate | 0.5 |
| Artemisia dry extract | 1.0 |
| Garlic dry extract | 1.0 |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A topically applicable stable oil-in-glycerin composition comprising a continuous glycerin phase, at least one vegetable oil, at least one biodegradable emulsifier and at least one bioactive essential oil component for topical, external use on skin and mucosal surfaces wherein the bioactivity of said essential oil is selected from the group consisting of topical anti-inflammatory activity, topical anti-fungal activity, topical anti-bacterial activity, topical anti-parasitic activity, and topical anti-viral activity, and wherein said essential oil is a volatile mixture of esters, aldehydes, alcohols, ketones, and terpenes.

2. A topically applicable stable oil-in-glycerin composition according to claim 1, wherein said emulsifier of vegetable origin is made by condensation of at least one vegetable fatty acid and a vegetable saccharide or disaccharide or poly-saccharide.

3. A topically applicable stable oil-in-glycerin emulsion composition according to claim 1, wherein said emulsion is substantially alcohol free.

4. A topically applicable stable oil-in-glycerin emulsion composition according to claim 1, wherein said glycerin constitutes a continuous phase of said emulsion and a minor portion of water is included in said glycerin phase.

5. A topically applicable stable oil-in-glycerin emulsion composition according to claim 1, wherein said vegetable oil is jojoba oil.

6. A topically applicable stable oil-in-glycerin emulsion composition according to claim 1, wherein said vegetable oil is a vegetable tryglyceride.

7. A topically applicable stable oil-in-glycerin emulsion composition according to claim 6, wherein said vegetable tryglyceride is a medium chain tryglyceride.

8. A topically applicable stable oil-in-glycerin emulsion composition according to claim 7, wherein said medium chain tryglyceride is a capric-caprylic tryglyceride.

9. A topically applicable stable oil-in-glycerin emulsion composition according to claim 8, wherein said capric-caprylic tryglyceride is fractionated coconut oil.

10. A topically applicable stable oil-in-glycerin emulsion composition according to claim 1, wherein said oil is present in an amount ranging from about 0.1–40 wt/wt %.

11. A topically applicable stable oil-in-glycerin emulsion composition according to claim 1, wherein said oil is present in an amount ranging from about 2–20 wt/wt %.

12. A topically applicable stable oil-in-glycerin emulsion composition according to claim 1, wherein said emulsifier is present in an amount ranging from about 0.1–20 wt/wt %.

13. A topically applicable stable oil-in-glycerin emulsion composition according to claim 1, wherein said emulsifier is present in an amount ranging from about 0.1–5 wt/wt %.

14. A topically applicable stable oil-in-glycerin emulsion composition according to claim 2, wherein said bioactive essential oil component is present in an amount ranging from about 0.1–20 wt/wt %.

15. A topically applicable stable oil-in-glycerin emulsion composition according to claim 1, wherein said emulsifier is substantially free of polyoxyethylene.

16. A topically applicable stable oil-in-glycerin emulsion composition according to claim 1, wherein said bioactive essential oil component has low water solubility.

17. A topically applicable stable oil-in-glycerin emulsion composition according to claim 1, for use in oral care.

18. A topically applicable stable oil-in-glycerin emulsion composition according to claim 1, for use in vaginal hygiene.

19. A topically applicable stable oil-in-glycerin emulsion composition according to claim 1, for veterinary use.

20. A topically applicable stable oil-in-glycerin composition comprising a continuous glycerin phase, at least one vegetable oil, at least one biodegradable emulsifier of vegetable origin made by condensation of at least one fatty acid with a vegetable carbohydrate or polycarbohydrate and at least one bioactive essential oil component for topical, external use on skin and mucosal surfaces wherein the bioactivity of said essential oil is selected from the group consisting of topical anti-inflammatory activity, topical anti-fungal activity, topical anti-bacterial activity, topical anti-parasitic activity, and topical anti-viral activity, and wherein said essential oil is a volatile mixture of esters, aldehydes, alcohols, ketones, and terpenes.

* * * * *